United States Patent
Fitz

(12)
(10) Patent No.: US 6,368,344 B1
(45) Date of Patent: Apr. 9, 2002

(54) STENT DEPLOYMENT SYSTEM WITH REINFORCED INNER MEMBER

(75) Inventor: Matthew J. Fitz, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/465,128

(22) Filed: Dec. 16, 1999

(51) Int. Cl.⁷ ............................................. A61M 25/01
(52) U.S. Cl. ..................... 623/1.11; 606/108
(58) Field of Search ............................. 623/1.11, 1.23; 606/108, 198; 604/264, 524, 525, 526, 527

(56) References Cited

U.S. PATENT DOCUMENTS

| | | |
|---|---|---|
| 5,026,377 A | 6/1991 | Burton et al. |
| 5,190,058 A | 3/1993 | Jones et al. |
| 5,201,757 A | 4/1993 | Heyn et al. |
| 5,290,295 A | 3/1994 | Querals et al. |
| 5,391,172 A | 2/1995 | Williams et al. |
| 5,507,768 A | 4/1996 | Lau et al. |
| 5,522,883 A | 6/1996 | Slater |
| 5,534,007 A | 7/1996 | St. Germain et al. |
| 5,540,712 A | 7/1996 | Kleshinski et al. |
| 5,556,426 A | 9/1996 | Popadiuk |
| 5,571,135 A | 11/1996 | Fraser et al. |
| 5,571,168 A | 11/1996 | Toro |
| 5,603,698 A | 2/1997 | Roberts et al. |
| 5,607,422 A * | 3/1997 | Smeets et al. ................ 606/41 |
| 5,643,278 A | 7/1997 | Wijay |
| 5,690,644 A | 11/1997 | Yurek et al. |
| 5,700,269 A | 12/1997 | Pinchuk et al. |
| 5,702,418 A | 12/1997 | Ravenscroft |
| 5,709,703 A | 1/1998 | Lukic et al. |
| 5,713,851 A * | 2/1998 | Boudewijn et al. ........... 604/35 |
| 5,725,571 A | 3/1998 | Imbert et al. |
| 5,733,267 A | 3/1998 | Del Toro |
| 5,772,668 A | 6/1998 | Summers et al. |
| 5,817,101 A * | 10/1998 | Fiedler ....................... 606/108 |
| 6,019,778 A * | 2/2000 | Wilson et al. .............. 606/198 |
| 6,070,589 A * | 6/2000 | Keith et al. ................ 606/198 |
| 6,264,671 B1 * | 7/2001 | Stack et al. ................ 606/198 |

* cited by examiner

*Primary Examiner*—Eduardo C. Robert
(74) *Attorney, Agent, or Firm*—Fulwider Patton Lee & Utecht, LLP

(57) ABSTRACT

A stent deployment system with a reinforced inner member is disclosed. The system has a self-expanding stent in a contracted condition disposed on the distal end of a delivery catheter and a retractable sheath covering the stent. The delivery catheter is advanced through a guide catheter to a desired location within a patient's body lumen. Once the stent is at the target site, the sheath is retracted by pulling back on the stem to expose the self-expanding stent. The reinforced inner member provides longitudinal compression resistance for the delivery catheter, while allowing for flexibility for navigation through a tortuous vasculature.

19 Claims, 3 Drawing Sheets

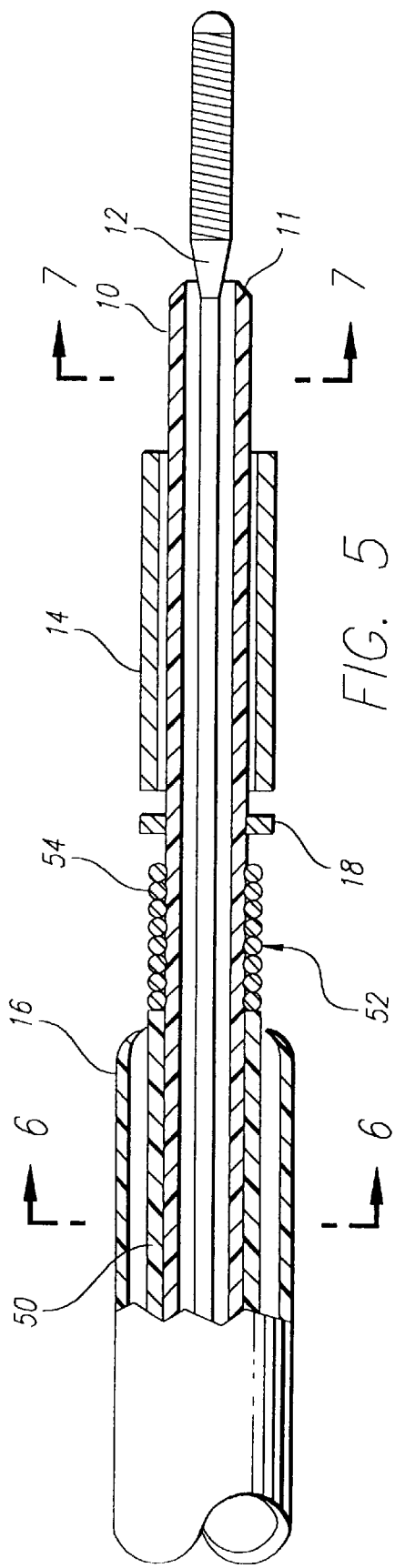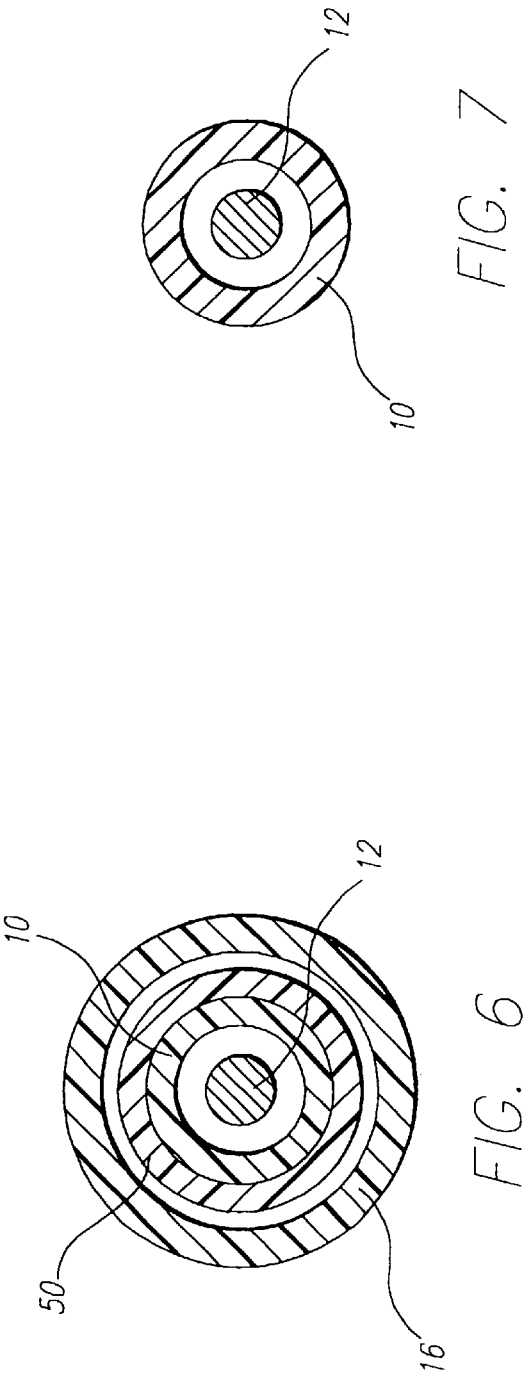

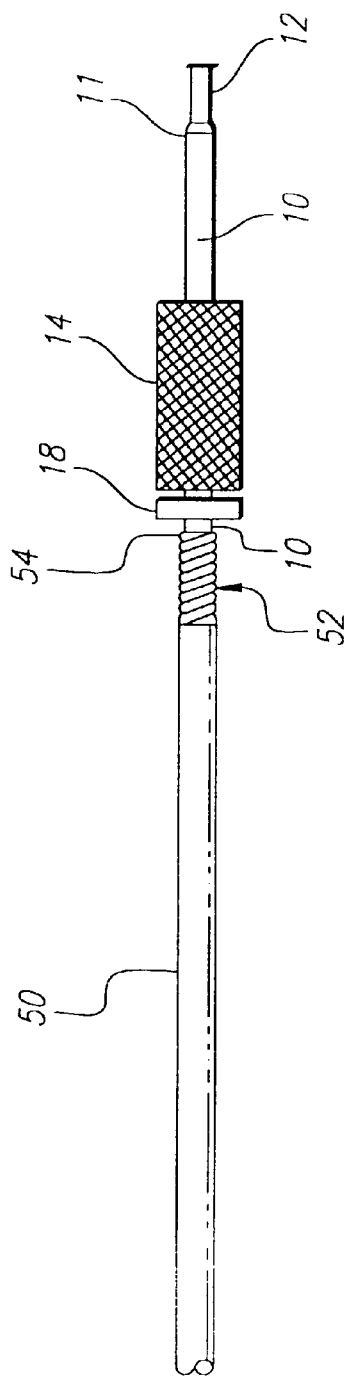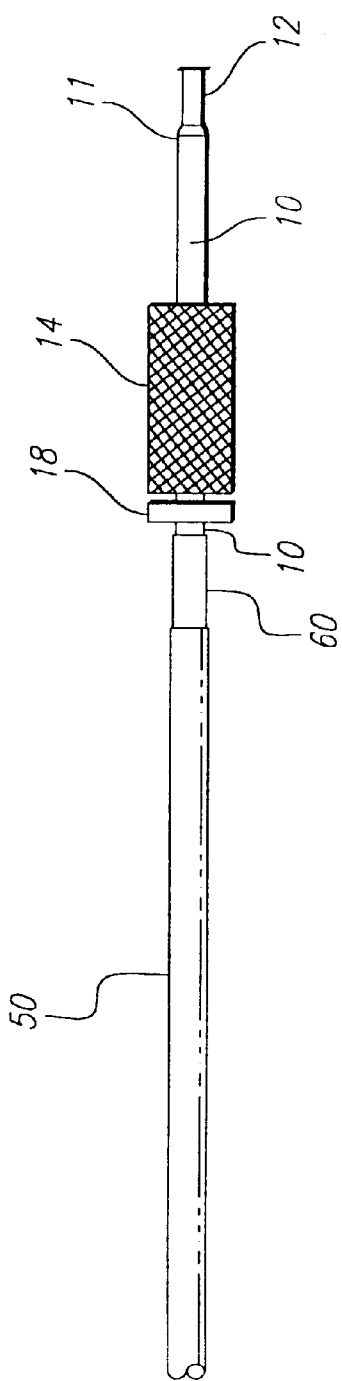
FIG. 8
FIG. 9

STENT DEPLOYMENT SYSTEM WITH REINFORCED INNER MEMBER

BACKGROUND OF THE INVENTION

The present invention relates in general to the delivery of stents into a body lumen, such as a blood vessel, to maintain the patency thereof. More particularly, the present invention relates to an improved stent delivery system that can accurately deliver a self-expanding stent within a body lumen.

In a medical procedure known as percutaneous transluminal coronary angioplasty (PTCA), a balloon catheter is used to dilate the lumen of a coronary artery which has become narrowed or restricted due to the accumulation of atherosclerotic plaque along the artery wall. In the PTCA procedure, a balloon catheter is advanced through the vasculature to the stenosis and the balloon is inflated to radially compress the atherosclerotic plaque against the inside of the artery wall. The balloon is then deflated so that the dilation catheter can be removed and blood flow resumed through the dilated artery.

Occasionally, the inflation of the balloon within the artery lumen will dissect either the stenotic plaque or the intima of the blood vessel or both. After the balloon is deflated and removed, blood can flow between the arterial wall and the dissected lining thereby constricting the flow passage or causing a section of the dissected lining, commonly called an "intimal flap," to be forced into the flow passageway. In the event of partial or total occlusion of an artery by a dissected arterial lining, the patient is put in an extremely dangerous situation requiring immediate medical attention.

Another problem which frequently arises after an angioplasty procedure is the appearance of a restenosis at or near the site of the treated artery. The restenosis may appear due to the accumulation of additional atherosclerotic plaque or may be the result of weakened arterial walls which have collapsed inward to restrict blood flow. When restenosis appears, the treated patient may require an additional angioplasty procedure or other treatment such as by-pass surgery, if an additional angioplasty procedure is not warranted.

Due to the problems caused by dissections of the arterial lining or the appearance of restenosis, much research has been performed on ways to maintain the patency of an artery after the angioplasty procedure is completed. In recent years, expandable endoprosthetic devices, commonly called "stents," have gained widespread acceptance as a means to support the arterial walls and maintain the patency of a treated vessel. Stents are generally cylindrically shaped intravascular devices which are placed within a damaged artery to hold it open and maintain unimpeded blood flow. Stents prevent dissected arterial linings from occluding an artery by pressing the dissected tissue against the arterial wall until natural healing results in the re-securing of the dissected tissue to the arterial wall. Stents also prevent the appearance of restenosis in the treated vessel by supporting the weakened arterial walls.

Various means have been developed for delivering and implanting intravascular stents within a body lumen. One common method involves compressing or otherwise reducing the diameter of a self-expanding stent, mounting the compressed stent on the distal end of a delivery catheter, placing a tubular sheath over the stent to restrain the stent in the contracted condition, and advancing the catheter through the patient's vasculature to the desired location. Once the stent is properly positioned, the stent is exposed by withdrawing the sheath proximally with respect to the stent, advancing the stent distally with respect to the sheath, or performing a combination of both. Once free from the sheath, the self-expanding stent expands against the arterial walls to thereby hold open the artery or other body lumen into which it is placed.

Other examples of stent delivery systems include U.S. Pat. No. 5,026,377 to Burton et al. Burton discloses an instrument for the deployment or retraction of a self expanding stent in a body canal, which comprises an elongated tubular outer sleeve having disposed therein an elongated core which is moveable relative to the sleeve and has a grip member formed at or near its distal end, which grip member is adapted to releasably hold a self-expanding stent within the outer sleeve. U.S. Pat. No. 5,190,058 to Jones et al. discloses a method of using a temporary stent catheter. The catheter comprises a catheter tube having a distal end and a proximal end; an elongated balloon inflatable by fluid pressure attached to the catheter tube near its distal end; a stent having a tubular configuration attached to the catheter tube near its distal end and surrounding the balloon; a pressurization device near the proximal end of the catheter tube for inflating and deflating the balloon, whereby the stent may be pressed against the wall of a blood vessel by the balloon and the balloon may be subsequently deflated; a restriction device near the proximal end of the catheter tube for maintaining the stent in an expanded condition and for subsequently effecting the radial contraction of the stent whereby it may be removed from the blood vessel.

U.S. Pat. No. 5,201,757 to Heyn et al. discloses an apparatus for deploying a radially self-expanding stent that includes proximal and distal sleeves respectively containing proximal and distal end portions of the stent in a reduced radius delivery configuration. Once the stent and sleeves are positioned at the intended fixation site, the sleeves are moved axially with respect to one another to permit radial self-expansion of the stent only over its medial region, while the sleeves continue to contain the axially outward regions of the stent. Upon sufficient movement of the sleeves axially relative to each other, the stent becomes totally free of the sleeves. U.S. Pat. No. 5,290,295 to Querals et al. discloses a tool for the intraluminal insertion and deployment of a tubular graft within a blood vessel, that is constructed from a flexible insertion shaft with a tapered distal end, a tubular sheath, a deployment slider and a safety locking tube.

U.S. Pat. No. 5,391,172 to Williams et al. discloses a stent delivery system with coaxial catheter handle. The catheter handle provides relative motion between the outer sheath of a stent delivery catheter and an underlying catheter, via a thumb switch, to enable the outer sheath to withdraw from over the underlying catheter and expose a vascular prosthesis.

U.S. Pat. No. 5,507,768 to Lau et al. discloses a stent delivery method and system that includes an elongated delivery sheath and a catheter disposed within an outer lumen of the sheath having an expandable member on its distal extremity. An expandable stent is mounted on the expandable member and the distal portion of the sheath tapers down and is tucked within an elastic cone during transport of the stent to a stenotic region. A manipulating device is provided on the proximal end of the delivery system to effect relative axial movement between the sheath and the catheter so as to expose the stent mounted on the expandable member on the catheter within a body lumen, such as a coronary artery, and allow the expansion of the stent by the expansion of the expandable member.

One of the difficulties with some prior stent deployment systems involves deploying the stent at the precise, desired location within the body lumen. Typically, a self-expanding stent is mounted on the distal end of a delivery catheter that is attached to a manipulator handle outside the patient's body. The stent is deployed by actuating a mechanism on the manipulator handle, such as a thumb plate, which is hand operated by the physician. When the thumb plate is withdrawn proximally relative to the manipulator handle, the sheath is withdrawn proximally relative to the catheter and stent.

Problems can arise when the sheath is retracted proximally by the application of a pulling force. The friction between both the stent and the sheath and the catheter and the sheath must be overcome by the pulling force in order for the stent to be deployed. The tensile force exerted on the outer sheath will be opposed by an equivalent compressive force exerted on the catheter. When compression of the catheter occurs, the sheath may not retract relative to the stent.

Alternatively, the sheath may retract after the catheter has already been compressed a certain amount. Consequently, the stent may not be deployed precisely in the desired location. Physicians have very little tolerance when it comes to inaccuracy of stent placement. A placement error of only millimeters is often considered to be intolerable. A poorly placed stent may do more harm than good and can be very difficult to retrieve once deployed. Therefore, it is critical to position the stent accurately on the first attempt.

A metal hypotube can be used throughout the length of the catheter to reinforce the catheter and increase the compression resistance of the catheter. However, the use of a hypotube at the distal end of the catheter can provide for a device that is generally not flexible enough to properly navigate through tortuous areas of the vasculature. Furthermore, some prior art attempts have produced catheters that are bulky and thick. These configurations may be prone to dislodging arterial plaque and are not ideal for navigation through a tortuous vasculature.

What has been needed and heretofore unavailable is a stent deployment system for self-expanding stents that provides a means to prevent unwanted movement of the stent and to provide greater accuracy of stent placement within a body lumen. The device should be highly resistant to compressive forces yet maintain enough flexibility for navigation through the highly tortuous vasculature. Additionally, the system should be relatively easy to use and manufacture. The present invention satisfies these needs and others.

As used herein, the terms "proximal," "proximally" and "proximal direction" when used with respect to the invention are intended to mean moving away from or out of the patient, and the terms "distal," "distally" and "distal direction" when used with respect to the invention are intended to mean moving toward or into the patient. These definitions will apply with reference to apparatus, such as catheters, guide wires, stents and the like.

SUMMARY OF THE INVENTION

The invention provides for a stent deployment system for delivering a self-expanding stent within a body lumen. The system provides for both resistance to longitudinal compression while at the same time retains adequate flexibility for navigation through a tortuous vasculature.

In one aspect of the invention, there is provided a stent deployment system for delivery of a self-expanding stent within a body lumen. The system includes a delivery assembly and a guide catheter. The delivery assembly includes an inner tubular member. The distal end of the inner tubular member is configured to receive over an exterior thereof the self-expanding stent. At least a portion of the inner tubular member includes a first reinforcing element connected thereto. The first reinforcing element provides longitudinal compression resistance for the inner tubular member, while allowing for flexibility for navigation through a tortuous vasculature. The delivery assembly also includes an elongated sheath formed with a lumen to slidably receive the inner tubular member. The guide catheter is formed with a lumen for receiving the delivery assembly therein.

The stent delivery system can be used to accurately deliver a stent to a desired location within a patient's vasculature system or other body lumen by preventing unwanted axial motion of the self-expanding stent during the deployment process. The stent delivery system is safe, easy-to-use and can be quickly and easily removed after the stent has been deployed. The present invention is designed primarily for use in the carotid arteries; however, the system also can be used to treat other vessels. Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 5 is a partial and magnified view, in partial longitudinal cross-section, the distal end of the stent delivery system of FIG. 3.

FIG. 6 is a transverse cross-sectional view taken along line 6—6 of FIG. 5, depicting the hypotube, catheter and guide wire contained within a lumen of the sheath.

FIG. 7 is a transverse cross-sectional view taken along line 7—7 in FIG. 5, depicting the guide wire slidably disposed within the catheter lumen.

FIG. 8 is a partial and elevational view of the present invention stent delivery system, depicting the first and second reinforcing elements.

FIG. 9 is partial and elevational view of an alternative embodiment of the present invention stent delivery system.

DETAILED DESCRIPTION OF THE PREFERRED EMBODIMENTS

Figure 1:
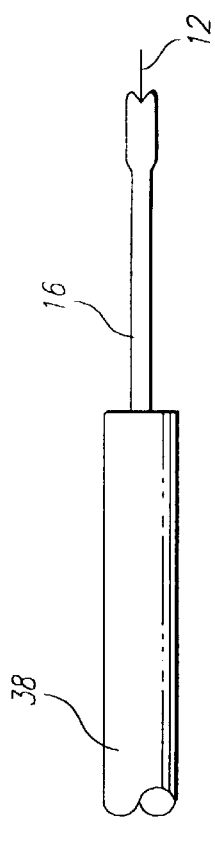
FIG. 1 is an elevational view of a preferred embodiment stent delivery system of the present invention.

As shown in the exemplary drawings wherein like reference numerals indicate like or corresponding elements among the figures, the present invention includes a stent deployment system for treating vessels in, for example, the carotid arteries and other vessels in the body. Frequently, after balloon angioplasty has been performed to dilate a stenosis in the lumen of a vessel, a self-expanding stent is deployed at the treated site to aid in the healing of dissected arterial lining and to prevent restenosis.

Typically, a self-expanding stent is delivered and deployed by first compressing the stent, mounting the stent at the distal end of a delivery catheter and slidably disposing the catheter and stent within the lumen of a sheath to hold the stent in a contracted condition. Once the catheter and stent are advanced to the desired location within a body lumen, the sheath is retracted to expose the self-expanding stent thereby allowing it to expand against the vessel wall. Examples of stent delivery systems are disclosed in, for example, U.S. Pat. Nos. 5,391,172 to Williams et al., and 5,507,768 to Lau et al., whose entire contents are hereby incorporated by reference.

As mentioned previously, in order to retract the sheath, the friction between both the stent and the sheath and the catheter and the sheath must be overcome by the pulling force used on the sheath. The tensile force exerted on the sheath will be opposed by an equivalent compressive force exerted on the catheter. When compression of the catheter occurs, one of two things may happen. The sheath may not retract relative to the stent. Alternatively, the sheath may retract after the catheter has already been compressed a certain amount. Consequently, the axial position of the stent might shift within the body lumen. This will cause the stent to be deployed in a different location than originally intended and thus not cover all of the target area. If the physician tries to compensate for the axial movement of the stent while attempting to retract the sheath, the physician may move the stent distally during deployment. This can cause the ends of the stent to tear into the body lumen wall.

The use of a metal hypotube throughout the length of the catheter can reinforce the catheter and increase the compression resistance of the catheter. However, the use of a hypotube at the distal end of the catheter can provide for a device that is generally not flexible enough to properly navigate through tortuous areas of the vasculature. It is therefore an object of the present invention to solve the accuracy problems associated with the prior art method of delivering and deploying self-expanding stents.

FIGS. 1–9 illustrate an exemplary stent deployment system that embodies features of the present invention. In the elevational views of FIGS. 1–4, the present invention delivery system includes an inner tubular member, such as delivery catheter 10, with a lumen therethrough adapted to receive a guide wire. The delivery catheter has proximal and distal ends and is configured to receive over an exterior thereof self-expanding stent 14. The stent preferably has superelastic (SE) characteristics and may be made of NITINOL® nickel-titanium alloy or any other suitable material. Stents are known in the art and stent 14 can be of any suitable design. A guide wire 12 is slidably disposed within a lumen of delivery catheter 10, and the stent is mounted on distal end 11 of the delivery catheter.

Figure 4:
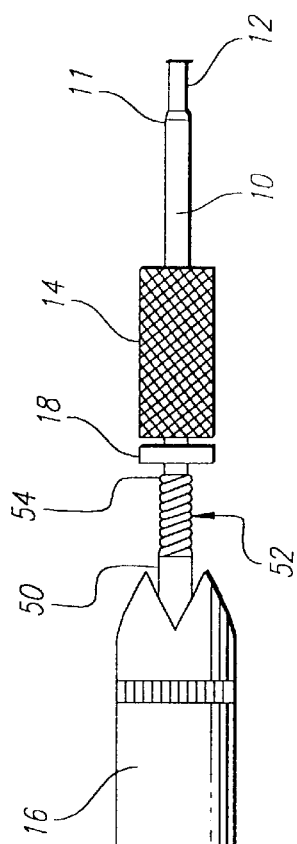
FIG. 4 is a partial and magnified view of the distal end of the stent delivery system depicted in FIG. 3.

As best seen in FIG. 4, delivery catheter 10 preferably has an elongated catheter body with at least one optional stop 18 that is immobile and located on a periphery near distal end 11 but proximally to stent 14 to prevent the stent from moving proximally relative to the delivery catheter. The stop can be an annular protrusion, a simple projection or the like to block the proximal movement of the stent.

The delivery catheter 10 and stent 14 are slidably disposed within elongated tubular sheath 16, that holds stent 14 in a contracted condition during advancement through the patient's vasculature. It is contemplated that the sheath can be formed with different shapes. A means can be provided, such as including a manipulator handle, at the proximal end of the delivery system to effect relative axial movement between the delivery catheter and the sheath. Some examples of means that can be used with the present invention in order to effect relative axial movement between the delivery catheter and the sheath are described in U.S. patent application Ser. No. 09/307,177 by Fitz entitled "STENT DELIVERY SYSTEM", filed, May 7, 1999, and U.S. patent application Ser. No. 09/313,780 by Stack et al. entitled "SELF-EXPANDING STENT WITH ENHANCED DELIVERY PRECISION AND STENT DELIVERY SYSTEM", filed May 17, 1999, which are incorporated herein in their entirety by reference. The novel features of the present invention can be used in conjunction with the inventions disclosed in these applications.

Figure 2:
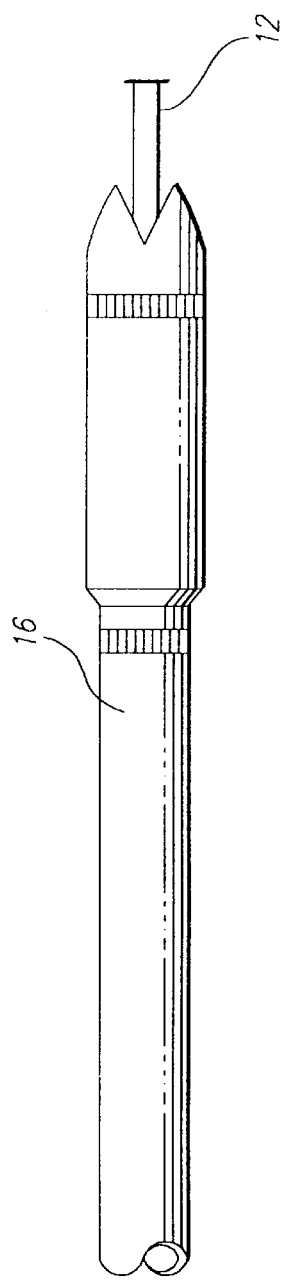
FIG. 2 is a partial and magnified elevational view of the distal end of the stent delivery system depicted in FIG. 1.
Figure 3:
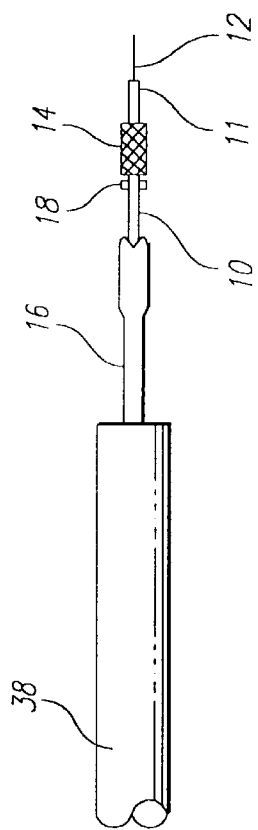
FIG. 3 is an elevational view similar to FIG. 1, but showing the sheath in its withdrawn position.

FIGS. 1 and 2 show the delivery assembly as it exists during advancement through the vasculature with elongated sheath 16 at least partially covering stent 14. The sheath has proximal and distal ends and is formed with a lumen to slidably receive delivery catheter 10. The sheath is formed with a cylindrical body of a first diameter and can include an open-ended receptacle, with a second diameter that is larger than the first diameter, at the distal end for receiving the stent. The sheath preferably has an inner diameter large enough to accommodate the delivery catheter and to allow free longitudinal movement therein. FIGS. 3 and 4 show the delivery system after sheath 16 has been withdrawn proximally relative to the delivery catheter to expose the stent.

FIG. 5 is a longitudinal cross-sectional view of distal end 11 of the delivery system after sheath 16 has been withdrawn to expose stent 14. FIGS. 6 and 7 show cross-sections of the delivery system wherein guide wire 12 is contained within the lumen of catheter 10 and the catheter is contained within a lumen of sheath 16.

Referring again to FIG. 3, guide catheter 38 has proximal and distal ends and is formed with a lumen for receiving the delivery assembly therein. The sheath 16, with delivery catheter 10 slidably disposed in its lumen, extends through the lumen of the guide catheter. The guide catheter facilitates the advancement of the stent delivery system through a patient's vasculature and has a diameter large enough to allow free longitudinal movement of the stent deployment system therein. The stent 14 is located in the desired axial position within a body lumen. The position of the delivery catheter, which is carrying the stent, is set precisely relative to the position of the guide catheter, using means discussed in the above-referenced patent applications. This in turn enables precise deployment of the stent at the target site. The delivery sheath can be made of conventional polyethylene tubing, or engineering polymers such as nylon, PEEK (polyethylene ethyl ketone) or PET (polyethylene terephthalate).

Referring now to FIGS. 4, 5, 6 and 8, at least a portion of delivery catheter 10 includes a first reinforcing element, such as coil 52, connected thereto at a location proximal to stop 18. The coil contains a plurality of windings 54. The coil is fixedly attached to the delivery catheter in a fully longitudinally compressed condition with the windings positioned in apposition with each other. Consequently, the coil provides longitudinal compression resistance for the delivery catheter, while allowing for flexibility for navigation through a tortuous vasculature. The coil can be made of metal such as such as stainless steel, NITINOL® nickel-titanium alloy or any other suitable material. In one embodiment, the coil can extend longitudinally for 10 to 15 cm in the compressed condition.

In one embodiment, delivery catheter 10 can be a tube constructed from polyethylene ("PE tube") or other suitable materials. The coil 52 can be wound around the delivery catheter using a standard winding technique, known to those skilled in the art. At least a portion of the delivery catheter can include a second reinforcing element such as hypotube 50 or another elongated tubular member, connected thereto.

The hypotube is positioned over and attached to the delivery catheter using glue or other suitable means. The hypotube is positioned such that it is proximal to the coil. After the coil and the hypotube are positioned over the delivery catheter, they can be configured so that they are in apposition with each other. The proximal end of the coil could be placed over the distal end of the hypotube end welded thereto.

Once hypotube 50 and coil 52 are positioned over delivery catheter 10, a heat-shrinkable tube can be placed over the device and then shrunk to secure the coil and hypotube to the delivery catheter. The hypotube provides further longitudinal compression resistance for the delivery catheter. The hypotube can be made of a rigid material such as metal. Preferably, the hypotube is made of stainless steel or NITINOL® nickel-titanium alloy for added kink resistance. As mentioned above, if the hypotube were used throughout the length of the catheter then the catheter may not have adequate flexibility. However, the coil fulfills at least two important functions. First, the coil will not compress longitudinally as it is already in a fully compressed condition. Second, the coil can bend, and therefore allows the catheter to bend. Thus, the coil provides added flexibility for navigation through a tortuous vasculature, while maintaining longitudinal compression resistance for the catheter.

Turning to FIG. 9, in an alternate embodiment, the first reinforcing element can be made of a rigid material, such as plastic, in the shape of tube 60. The tube can be made of polyimide or PEEK, in one embodiment. The tube 60 is fixedly attached to delivery catheter 10 at a location proximal to stop 18. Consequently, tube 60 provides longitudinal compression resistance for the delivery catheter, while allowing for flexibility for navigation through a tortuous vasculature. In one embodiment, tube 60 can extend longitudinally for 10 to 15 cm.

In operation, guide catheter 38 is percutaneously introduced into the cardiovascular system of a patient through, for instance, the femoral artery, and is advanced therein until the distal tip thereof is just proximal of the vessel site to be treated. The stent deployment system is introduced through guide catheter 38 with guide wire 12 slidably disposed within the lumen of delivery catheter 10. Upon reaching the distal end of the guide catheter, the guide wire is extended out from catheter 10 and is advanced to the target site. Thereafter, catheter 10 and stent 14 are advanced over guide wire 12, such as by manipulating a manipulator handle or other appropriate device, until the stent is positioned at the desired location. The position of the stent mounted on the distal end of the delivery catheter is fixed relative to guide catheter 38, as mentioned above, and therefore the two should remain stationary within the body lumen, even during stent deployment.

To deploy self-expanding stent 14, the physician, while using a fluoroscope to view the treated site, withdraws sheath 16 proximally relative to both catheter 10 and self-expanding stent 14. In the same motion that the sheath is withdrawn proximally, the stent is prevented from sliding proximally along catheter 10 by at least one immobile stop 18 located on the periphery of catheter 10.

With sheath 16 withdrawn, self-expanding stent 14 is no longer restrained in a contracted state and expands against the vessel walls. After the stent has fully deployed, the delivery system is withdrawn from the patient's body with the stent remaining in the vessel lumen to maintain the patency of the treated vessel.

From the foregoing, it will be appreciated that the stent delivery system of the present invention allows self-expanding stents to be deployed while preventing any unwanted axial movement of the stent. The invention is made of materials commonly found in the industry and is simple to use and easy to manufacture.

While the invention herein has been illustrated and described in terms of a stent deployment system with a reinforced inner member, it will be apparent to those skilled in the art that the invention can be used in other instances. Other modifications and improvements may be made without departing from the scope of the invention.

What is claimed:

1. A stent deployment system for delivery of a self-expanding stent within a body lumen, comprising:
   a delivery assembly including
      an inner tubular member having a proximal end and a distal end, the distal end configured to receive over an exterior thereof the self-expanding stent;
      wherein at least a portion of the inner tubular member includes a first reinforcing element connected thereto, the first reinforcing element providing longitudinal compression resistance for the inner tubular member, while allowing for flexibility for navigation through a tortuous vasculature; and
      an elongated sheath having a proximal end and a distal end and formed with a lumen to slidably receive the inner tubular member; and
   a guide catheter having a proximal end and a distal end, and formed with a lumen for receiving the delivery assembly therein.

2. The system of claim 1, wherein the first reinforcing element is a coil.

3. The system of claim 2, wherein the coil is fully compressed.

4. The system of claim 1, wherein the first reinforcing element is made of metal.

5. The system of claim 1, wherein the first reinforcing element is made of a rigid material in the shape of a tube.

6. The system of claim 5, wherein the first reinforcing element is made of plastic.

7. The system of claim 1, wherein the first reinforcing element adapted to be located proximal to the stent.

8. The system of claim 1, wherein at least a portion of the inner tubular member includes a second reinforcing element connected thereto, the second reinforcing element providing longitudinal compression resistance for the inner tubular member.

9. The system of claim 8, wherein the second reinforcing element is an elongated tubular member.

10. The system of claim 9, wherein the second reinforcing element is positioned over and attached to the inner tubular member.

11. The system of claim 8, wherein the second reinforcing element is made of a rigid material.

12. The system of claim 11, wherein the second reinforcing element is made of metal.

13. The system of claim 8, wherein the second reinforcing element is proximal to the first reinforcing element.

14. The system of claim 13, wherein the second reinforcing element comes into apposition with the first reinforcing element.

15. The system of claim 1, wherein the elongated sheath is formed with a cylindrical body of a first diameter and has an open-ended receptacle at the distal end for receiving the self-expanding stent;
   and wherein the receptacle has a second diameter larger than the first diameter.

16. The system of claim 1, wherein the inner tubular member further has an inner lumen adapted to receive a guide wire therethrough.

17. The system of claim 1, wherein a stop is disposed on an exterior of the inner tubular member adapted to be proximal to the self-expanding stent and distally to the first reinforcing element to prevent the stent from moving proximally during relative movement between the sheath and the inner tubular member.

18. The system of claim 17, wherein the stop includes an annular shape.

19. The system of claim 1, wherein the inner tubular member is a delivery catheter.

* * * * *